United States Patent [19]

Drescher-Krasicka

[11] Patent Number: 5,307,680
[45] Date of Patent: May 3, 1994

[54] METHOD AND APPARATUS FOR VISUALIZATION OF INTERNAL STRESSES IN SOLID NON-TRANSPARENT MATERIALS BY ELASTOACOUSTIC TECHNIQUE

[75] Inventor: Ewa Drescher-Krasicka, Gaithersburg, Md.

[73] Assignee: The United States of America as represented by the Secretary of Commerce, Washington, D.C.

[21] Appl. No.: 964,598

[22] Filed: Oct. 21, 1992

[51] Int. Cl.$^5$ .................... G01N 29/04; G01N 3/08; G01H 1/08
[52] U.S. Cl. ...................................... 73/606; 73/600; 73/818
[58] Field of Search ................ 73/606, 607, 599, 600, 73/626, 620, 624, 646, 581, 528, 629, 597, 598, 788, 818, 801

[56] References Cited

U.S. PATENT DOCUMENTS

| | | |
|---|---|---|
| 4,012,951 | 3/1977 | Kessler . |
| 4,459,852 | 7/1984 | Chubachi et al. ............ 73/606 |
| 4,503,708 | 3/1985 | Kino et al. . |
| 4,524,621 | 6/1985 | Yamanaka ................. 73/606 |
| 4,531,410 | 7/1985 | Crostack . |
| 4,620,443 | 11/1986 | Khuri-Yakuh .............. 73/606 |
| 4,655,083 | 4/1987 | Chubachi .................. 73/606 |
| 4,658,649 | 4/1987 | Brook ..................... 73/598 |
| 4,674,333 | 6/1987 | Jindo et al. . |
| 4,702,112 | 10/1987 | Lawrie et al. .............. 73/606 |
| 4,788,866 | 12/1988 | Tanimoto et al. . |
| 4,866,986 | 9/1989 | Cichanski . |
| 5,079,952 | 1/1992 | Nakaso et al. .............. 73/624 |
| 5,085,081 | 2/1992 | Ohn ....................... 73/606 |

OTHER PUBLICATIONS

Curtis, G. J., "The Use of Surface Elastic Waves in Examing Surface Mechanical Properties", Sziland, J., *Ultrasonic Testing* (N.Y., Wiley, 1982), pp. 326-340.
R. A. Toupin and B. Bernstein, J. Acoust. Soc. Am. 33, pp. 216-225, 1961, "Sound Waves in Deformed Perfectly Elastic Materials, Acoustoelastic Effect".
R. N. Thurston and K. Brugger, Phys. Rev., vol. A133, pp. 1604–1610, 1964, "Third-Order Constants and the Velocity of Small Amplitude Elastic Waves in Homogeneously Stressed Media".
D. I. Crecraft, J. Sound Vib. 5, (I), pp. 173–192, 1967, "The Measurement of Applied and Residual Stresses in Metal Using Ultrasonic Waves".
N. N. Hsu, Experimental Mech. vol. 14, No. 5, pp. 169–176, 1974, "Acoustical Birefringence and the Use of Ultrasonic Waves for Experimental Stress Analysis".
Yih-Hsing Pao, Tsung-Tsong Wu and U. Gamer, J. App. Mech., pp. 11–17, vol. 58, 1991, "Acoustoelastic Birefringence in Plastically Deformed Solid".
J. H. Cantrell and K. Salama, Intern. Mat. Rev., vol. 36, 1991, pp. 125–145, "Acoustoelastic Characterisation of Materials".

(List continued on next page.)

Primary Examiner—John E. Chapman
Assistant Examiner—Helen Kwok
Attorney, Agent, or Firm—Jacobson, Price, Holman & Stern

[57] ABSTRACT

A process and apparatus for visualization of internal stresses in solid materials by an acoustic microscope (10) connected to an acoustic lens (5) having a circular or spherical transmitting and receiving surface (8) for transmitting ultrasonic waves to and receiving reflected waves from a sample (3) to be examined in a body of liquid (2), such as water, a motor drive unit (7) having a movable arm thereon (6) connected to the acoustic lens (5) for supporting and moving the lens for scanning the sample, the motor drive (7) being connected to the acoustic microscope (10) for being operated thereby to perform the scanning, a computer (16) having a visual display unit (18), and an oscilloscope (20) for indicating the reflected waves.

20 Claims, 14 Drawing Sheets

OTHER PUBLICATIONS

G. S. Kino et al., J. Appl. Phys. vol. 50, pp. 2607–2613, 1979, "Acoustoelastic Imaging of Stress Fields".

G. C. Johnson, J. Appl. Mech. vol. 48, 1981, pp. 791–795, "On the Applicability of Acoustoelasticity for Residual Stress Determination".

S. W. Meeks et al., Appl. Phys. Lett. vol. 55, No. 18, pp. 1835–1837, 1989, "Microscopic Imaging Residual Stress Using a Scanning Phase-Mesauring Acoustic Microscope".

J. H. Cantrell and M. Qian, Appl. Phys. Lett. vol. 57, No. 18, 1990, pp. 1870–1872, "Scanning Electron Acoustic Microscope of Indentation Induced Cracks and Residual Stresses In Ceramics".

K. F. Young, IBM J. Res. Develop. vol. 34, No. 5, 1990, pp. 706–717, "Finite Element Analysis of Planar Stress Anisotropy and Thermal Behavior in Thin Films".

Uniaxial Compression
$\sigma_1 \neq 0, \sigma_2 = \sigma_3 = 0$

Biaxial Compression
$\sigma_1 \neq 0, \sigma_2 \neq 0, \sigma_3 = 0$

METHOD AND APPARATUS FOR VISUALIZATION OF INTERNAL STRESSES IN SOLID NON-TRANSPARENT MATERIALS BY ELASTOACOUSTIC TECHNIQUE

BACKGROUND OF THE INVENTION

This invention relates to the detection and mapping of internal stresses in the interior of bulk materials by scanning acoustic technique.

It is known to utilize an ultrasonic microscope to compare a plurality of images detected by the ultrasonic waves reflected on or passing through a sample under different conditions by displaying the images on a cathode ray tube, such as shown in U.S. Pat. No. 4,674,333. It is also known to use a scanning acoustic microscope (SAM) for inspection and quality control in manufacturing and other industrial applications wherein the object under investigation is insonified by ultrasonic acoustic pulses, and ultrasonic reflections from the object are received and utilized to generate electrical signals which are used to develop an image of the object, the device being capable of focusing on varying transition levels within the object, as shown in U.S. Pat. No. 4,866,986. It is known from this latter patent that when an acoustic pulse encounters any discontinuity (change of the acoustic impedance of the medium through which it is traveling), part of its energy is reflected and it is these echoes that a reflection mode acoustic microscope receives and eventually employs to display an image of internal features of the target object. Various types of information are present in the returned or echo pulses. For example, the time delay between radiation and reception provides an accurate index of the depth, or distance in the direction of travel, of a discontinuity.

The use of acoustic microscopy for nondestructive examination of materials is also shown in the following U.S. Pat. Nos. 4,531,410; 4,702,112; and 4,788,866. These are incorporated herein by reference.

The use of acoustic microscopy for nondestructive testing of internal physical characteristics of bodies of metal and ceramic materials is also described in copending U.S. patent application Ser. No. 07/922,845, filed Jul. 31, 1992, in which the applicant is a joint inventor.

Characteristic features of acoustic microscopes are also described in the following U.S. Pat. Nos.: 4,503,708; 4,459,852; and 5,079,952, for example. All of the above prior patents are incorporated herein by reference as showing known structural and functional features of acoustic microscopes used in nondestructive examination of bodies of materials.

None of the above prior art, however, teaches a method and apparatus for visualizing by acoustic microscope imaging the internal stresses in the volume of solid transparent and non-transparent to light materials.

Although acoustic birefringence is well known in the literature, the attention of researchers has been attracted to the techniques of measuring the effect of stresses on acoustic velocity. The acoustic elastic effect, or the sensitivity of velocity of particular modes to applied stresses, has been used by investigators for imaging the stress field in metals. Benson and Raelsen proposed this method and reported the experimental data of the effects of stress on acoustic velocity in simple compression (R. W. Benson and V. J. Raelson, Product. Eng. 30. Acousto-elasticity, 1959). In analogy to photoelasticity, they found birefringence to be proportional to the difference of two principal stresses in a plane specimen. Toupin and Bernstein (R. A. Toupin and B. Bernstein, J. Acoust. Soc. Am. 33, 216, 1961) derived the relations for acoustoelastic effects and determined the third order elastic constants of an isotropic material. Thurston and Brugger (R. N. Thurston and K. Brugger, Phys. Rev., Vol. A133, (1604-1610) 1964) discussed, in general, the wave propagation in a strained material. Hughes and Kelly (D. S. Hughes and J. L. Kelly, Phys. Rev. 92, 5, 1953) derived expressions for elastic wave velocities in terms of the Murnagham third order elastic constants l, m,, n, for the case of a normally isotropic body, taking the Lamé constants $\mu$ and $\lambda$, as the second order coefficients. Crecraft (D. I. Crecraft, J. Sound Vib. 5, (I),(173-192), 1967) compared photoelasticity and "sonoelasticity" and presented the results of measurements of stress-induced velocity variations of both longitudinal and shear ultrasonic waves to megacycle frequencies. Data are provided for Polystyrene, Armco-Iron, Pyrex, Nickel-Steel, Copper (99.9%) and Aluminum (99%). Hsu (N. N. Hsu, Experimental Mech. Vol. 14, No. 5, (169-176), 1974) applied the pulse overlap technique for velocity measurements increasing the accuracy compared to "singaround" technique used by Crecraft. However difficulties were encountered when an attempt was made to apply acoustoelastic theory with ultrasonic measurements of residual stresses. The most recent theories (Yih-Hsing Pao, Tsung-Tsong Wu and U. Gamer, J. App. Mech. Vol. 58/11 1991) take into account the effects of plastic deformation, texture and other sources of anisotropy in materials. Recently, velocity changes were monitored by many investigators for stress imaging in metals (J. H. Cantrell and K. Salama, Intern. Mat. Rev., Vol. 36, No. 4, 1991; G. S. Kino et al., J. Appl. Phys. Vol. 50, (2607-2613), 1979; G. C. Johnson, J. Appl. Mech. Vol. 48/791, 1981; M. Hirao and Yih-Hsing Pao, J. Acoust. Soc. Am, Vol. 77 No. 5, 1985; S. W. Meeks et al. , Appl. Phys. Lett. Vol. 55, (18) 1989; J. H. Cantrell and M. Qian, Appl. Phys. Lett. Vol. 57, No. 18, 1990) and ceramics (K. F. Young, IBM J. Res. Develop. Vol. 34, No. 5, 1990).

Although the effect is small (less than 1%), many very elaborate and precise efforts were made to image velocity change on both macroscopic and microscopic scale in order to obtain the information on distribution of stresses mostly in the areas close to the surface of the sample.

BRIEF SUMMARY OF THE INVENTION

It is an object of this invention to provide a method of detecting and mapping internal stresses in the interior of isotropic bulk materials.

It is a further object of this invention to provide a method and apparatus for visualizing internal stresses in solid transparent and non-transparent materials by acoustic microscopy.

The above objects are attained in the instant invention by a novel method and apparatus for imaging by acoustic microscopy internal stresses in the interior of solid materials by utilizing polarized acoustic modes in the received signal. The acoustic birefringence effect caused by internal stresses can be explained as a splitting of a polarized shear mode propagating through a locally anisotropic volume of the material into two or more differently polarized shear modes having different velocities. The acoustic waves propagating in the stressed volume show the trirefringence effect, which adds to the two polarized shear modes a polarized longitudinal wave. An acoustic microscope image is produced using each of these modes separately, or by gating several polarized wave arrivals. The change of the polarization angle of the shear acoustic modes is detected in an acoustic microscope technique as a change in the intensity of the received signal. In the invention, every shear mode created by mode conversion of a longitudinal refracted wave at a water-solid interface is polarized. When, the material is stressed over a localized region, following the analogy to optics, in the stressed areas, the polarized shear mode will experience the change of intensity caused by birefringence effect. The shear wave will split into two, mutually perpendicular polarized components propagating with different speed inside the stressed area. This wave will suffer the change of the intensity in comparison with the intensity of the arrivals from isotropic, stress free volume. The acoustic waves show trirefringence effect, because the speed of longitudinal waves is also affected by acting stress.

The stress detection is based on the sensitivity of the direction of polarization of shear acoustic modes to a local acoustic anisotropy. The intensity of the polarized waves changes with the degree of inherent stress in the samples, and with the degree of applied stress in the samples produced by subjecting the samples to tension or compression load. The simplest ray analyses of transmitted and received pulses based on Snell's law explains the applicability of this scanning acoustic approach to internal stress mapping. With a broad range of available acoustic wave lengths, varying from a few microns to tenths of millimeters, the invention is applicable to many practical problems, such as the detection of internal stresses produced by fabrication of metals or ceramics.

The change of the polarization angle of the shear acoustic mode detected in the instant invention results in the interference patterns or local changes of the intensity of the acoustic image whenever the acoustic beam travels through the locally anisotropic volume of material. The interference pattern can be significantly enhanced by the interference with the leaky modes between water and the surface of the material being examined, but the presence of the internal stresses can be detected and seen or visualized also without the interference with the surface leaky mode.

By monitoring the intensity of polarized modes one can map stresses (internal or caused by external load) in the interiors of solid materials. This technique is based on comparison of the amplitudes of polarized modes propagating through locally anisotropic areas and through stress-free volumes of the sample. The presence of internal stresses in the interior of isotropic, bulk materials might be understood, in analogy to optics, as a temporary or artificial double refraction.

In optics, many non-crystalline transparent materials which are ordinarily optically isotropic become anisotropic and display optical characteristics similar to single crystals when they are stressed. This effect normally persists while the stress loads are maintained, but vanishes almost instantaneously when the stresses are removed. This phenomenon is known as temporary or artificial double refraction and was first observed by D. Brewster in 1816 in optical, transparent to light materials. The corresponding effect in acoustics is known as acoustic birefringence or trirefringence in anisotropic single crystals as well as in isotropic materials subjected to stress.

In the analogy between polarized light and polarized shear mode in acoustics, it should be noted that every shear mode created in acoustic microscopy by mode conversion at a water-solid interface at incident angles of the spherical lens, is polarized. Following the analogy to the experiment in optics, with the polarizer and analyzer, in the stressed areas the polarized shear acoustic mode will experience the change of the polarization angle caused by birefringence effect, splitting into two mutually perpendicular polarized waves. In this manner every shear mode propagating through the locally stressed (i.e. locally anisotropic interior) of the bulk sample will suffer the change of the intensity (in comparison with the intensity of the arrivals from the isotropic stress free volume) due to the birefringence split. Only modes polarized perpendicularly, or under the angle not equal to 0° or 180°, to the surface of the sample will convert back, into the longitudinal wave in water, and will be detected by the acoustic lens.

Acoustic modes will show the trirefringence effect, which adds to the shear wave split, the quasi-longitudinal polarized wave which can propagate in one of the directions of the crystallographic axis. In general, it can be said that the acoustic technique is more complicated than the optical temporary birefringence.

The elastoacoustic technique of this invention is non-presently existing in techniques such as: optical metallography, optical microscopy, X-ray diffraction or photoelasticity.

Acoustic microscope imaging of internal stresses inside the volume of the sample in accordance with the invention involves:

(a) choosing a polarized shear mode in the received signal from the defocused acoustic lens. This could be the reflection from the back surface or scattered arrivals from the discontinuities inside the material.

(b) separation of the chosen signal from other arrivals and using it for imaging the area beneath the surface.

By analogy to elastooptics the internal stresses can be analyzed based on the interference or intensity patterns of the elastoacoustic images.

This invention can be used for the detection of internal stresses produced by the fabrication of metals or ceramics without the existing limitation to the very small area of X-ray or optical microscope, or to the small sizes of the samples.

The elastoacoustic stress detection of the invention can be used for verification of existing theoretical models predicting the stress and strain fields under load.

BRIEF DESCRIPTION OF THE DRAWINGS

The invention will now be described in greater detail with reference to the accompanying drawings wherein.

DETAILED DESCRIPTION

Figure 1:
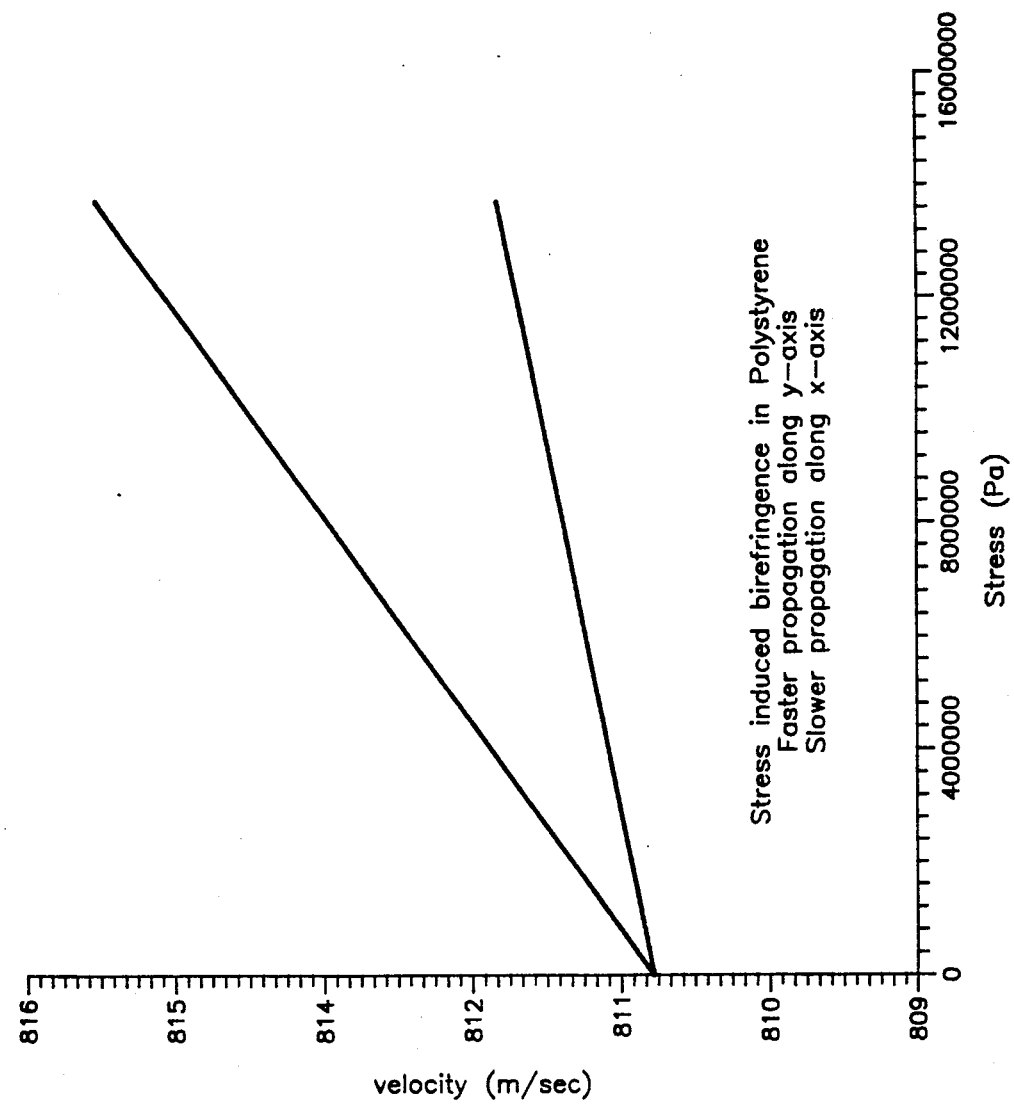
FIG. 1 is a diagram showing calculated stress induced birefringence in Polystyrene. These values can also describe in approximation the behavior of PMM. Estimated from the Vickers hardness test the yield strength for the samples used in the described experiment ranged between 6 and 12 MPa. The stress during the experiment was calculated based on the known value of the load (measured deformation of calibrated springs) over the area of the samples. At known value of the applied stress (5.8 MPa the velocities of faster component $c_1 = 812.33$ m/sec. and slower component $c_2 = 811.20$ m/sec. Without the exact data of the second and third order elastic constants for Plexiglass the estimated values have approximate character.

When a body is subjected to any three dimensional stress system, there exits at every point within the body three mutually perpendicular planes across which the resultant stress is normal. The normal stresses acting on these planes are the principal stresses and their directions correspond to the principal crystallographic axes in an anisotropic crystal. In general, the three principal stresses at a point are all different. If two of the principal stresses are equal, or zero as in the case of a thin rod subjected to a simple longitudinal tension or compression, the material at that point behaves as a uniaxial crystal of the tetragonal system. If the three principal stresses are all equal as in the case of pure hydrostatic compression, the material may be regarded as corresponding to a crystal in the cubic or isometric system, and the birefringence produced is zero.

The optical properties of material were described by equations formulated by Maxwell in 1852 which express the relationships between the principal refractive indices m and the principal stresses:

$$m_1 - m_2 = C(\sigma_1 - \sigma_2)$$
$$m_2 - m_3 = C(\sigma_2 - \sigma_3)$$
$$m_3 - m_1 = C(\sigma_3 - \sigma_1)$$

in which C is a constant depending on the material.

Formally derived theory for the acoustoelasticity was written by Toupin and Bernstein [supra] and Thurston and Brugger [supra]. They determined the basic relations of the acoustoelasticity based on infinitesimal wave propagation in a deformed isotropic elastic material. This results in the three polarization directions which are perpendicular to each other and in general, do not coincide with one of the principal axes of stress. When the propagation direction coincides with one of the principal axes of stress the former are identical to the latter and the magnitude of the acoustical birefringence is proportional to the difference of the secondary principal stresses. In the case of polarized longitudinal waves the difference between the velocity in unstressed and stressed material is proportional to the sum of the secondary principal stresses.

Inserting an arbitrary polarized shear ultrasonic wave into a deformed specimen in a two-dimensional stress state, the wave is separated into two linearly polarized waves, whose directions are the principal axes of the stress. Due to the phase difference between the two components at the other end of the sample the creative or destructive interference might take place, if the multiple wave length is matching the length of the travel path through the thickness of the sample.

The change of speed of sound in undeformed Cio and deformed Cly material can be expressed as:

$$\frac{C_{10} - C_{1y}}{C_{10}} = B(\sigma_1 + \sigma_2) \quad (1)$$

$$\frac{C_{2y} - C_{2x}}{C_{20}} = B(\sigma_1 - \sigma_2) \quad (2)$$

The first subscript 1, refers to longitudinal waves and 2 refers to shear waves. The second subscript refers to the direction of the applied compresional stress, and B is an acoustoelastic constant dependent on materials properties, in analogy to elastooptic constant C and can be expressed (G. C. Johnson, J. Appl. Mech. Vol. 48/791, 1981) in terms of Lame M, I and Murnagham constants l, m, and n as $$B = \frac{\mu l - \lambda(m + \lambda + 2\mu)}{\mu(3\lambda + 2\mu)(\lambda + 2\mu)} \quad (3)$$

In analogy to optics the sonoelastic constants B are needed for every material tested in order to quantitize the values of the stress at every point of the image. The advantage of this technique over optical methods is digitized form of the stored data.

Presented acoustic imaging of stresses monitors the change of the amplitudes of polarized shear and longitudinal waves caused by temporary anisotropy. The obtained acoustic images show the stress pattern in the plane samples of the tested materials, and the results are similar to elastooptics. The existing acousto-elastic theories are formulated for "velocity-stress" approach. In order to quantitize information on distribution and state of stress in uniaxially or biaxially deformed plane samples one has to calibrate the monitored intensities of the stress patterns as a function of stress values and stress distribution.

Hughes and Kelly (D. S. Hughes and J. L. Kelly, Phys. Rev. 92, 5, 1953) derived the expressions for elastic wave velocities in terms of Murnagham third order elastic constants l, m, and n, for the case of a normally isotropic body taking the Lamé constants and $\lambda$, $\mu$ as second order coefficients.

Figure 2:
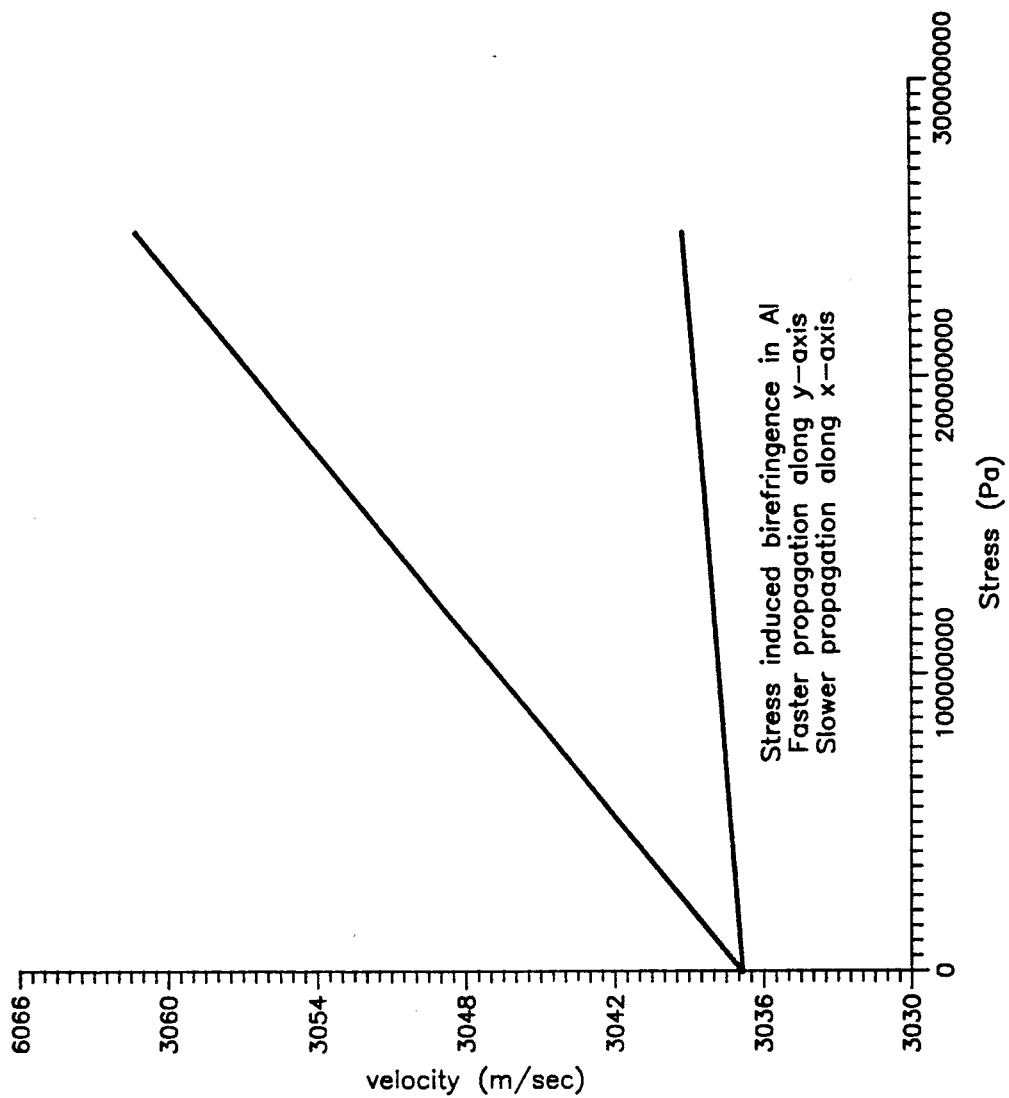
FIG. 2 is a diagram showing calculated stress induced birefringence in aluminum as a function of increasing stress. All aluminum samples were cut from a cold rolled sheet of 6061-0 and 2024-0 heat treated aluminum. The applied stress in order of 5.5 MPa added to the internal stresses in the aluminum samples. Annealing and slow cooling did not remove the internal stresses. In the observed stress patterns the range of significant amplitude variations is expected when the phase angle difference between the two split components is greater then 30°. The phase difference depends on the values of the applied stress and the path length in the stressed volume of the sample. For the known value of stress the path length x, can be calculated from eq. (5)

Three of these expressions for simple uniaxial stress are:

$$P_o C_{1y}^2 = \lambda + 2\mu - \frac{T}{3K_o}\left[2l - \frac{2\lambda}{\mu}(m + \lambda + 2\mu)\right] \quad (3a)$$

$$P_o C_{2y}^2 = \mu - \frac{T}{3K_o}\left[m + \frac{\lambda n}{4\mu} + \lambda + 2\mu\right] \quad (3b)$$

$$P_o C_{2x}^2 = \mu - \frac{T}{3K_o}\left[m - \frac{(\lambda + \mu)}{2\mu}n - 2\lambda\right] \quad (3c)$$

where $P_0$ is the density and $K_0 = \lambda + 2\mu/3$ is the bulk modulus, under zero stress conditions; T is the uniaxial compressive stress, which is applied in the direction given by the second subscripts on the velocities; of the first subscripts, 1 refers to longitudinal waves and 2 refers to shear waves, the latter being polarized in the Y direction. Propagation is in the X direction in all cases. The equations (3b) and (3c) were plotted for the materials of interest (aluminum, plexiglass) based on Crecraft's experimental data for the Murnagham constants and Lame constants as a function of increasing stress. The results are shown in FIGS. 1 and 2.

The velocity difference between the two split components of polarized shear modes increase linearly with increasing stress. The ending stress values were taken as a multiple of the yield stress. For aluminum and copper sheets, where the yield strength depends strongly on thermal and mechanical treatment one can expect the variations of yield stress from 4 MPa up to 300 MPa. There are also variations of the yield stress in plexiglass. The numbers shown in FIGS. 1 and 2 were calculated for the isotropic pure aluminum, without texture, residual stresses and plastic deformations in aluminum and without thermal internal stresses or previous plastic deformation for Polysterene, and under the assumption, that the state of stress is uniaxial.

For observed temporary birefringence in plexiglass and aluminum the calculated stress values were related to the increasing phase angle between two split components of shear waves which is proportional to the traveled distance X in the material.

The observed amplitude change in acoustic imaging of stress is a sum of two progressing coherent harmonic waves with two different wave vectors $k_1$, and $k_2$, the sum can be expressed as:

$$\cos(k_1 x - wt) + \cos(k_2 x - wt)$$

and might be rewritten as:

$$2\cos\left[\left(\frac{k_1 + k_2}{2}\right)x - \omega t\right]\cos\left[\frac{(k_2 - k_1)}{2} x\right] \quad (4)$$

the first component of equation (4) will change rapidly, the second component will change slowly. From the second component one can evaluate the traveling distance X at the assuming phase angle $2\pi$;

because $(k_1 - k_2) << (k_1 + k_2)$ \quad (5)

$$x = \frac{4\pi}{k_2 - k_1} = \frac{2\lambda_1\lambda_2}{\lambda_1 - \lambda_2}$$

where $k_1 = \frac{2\pi}{\lambda_1}$ and $$k_2 = \frac{2\pi}{\lambda_2}; \quad \lambda_1 = \frac{c_1}{f}; \quad \lambda_2 = \frac{c_2}{f}$$

The frequency f used in the measurements was 10 MHz, and the velocity values c, and c at the applied level of stress can be obtained from FIG. 1 and 2, according to equation (3) for aluminum, copper and plexiglas from Crecraft (D. I. Crecraft, J. Sound Vib. 5, (I), (173-192), 1967) data under assumption, that the stress acting on sample is uniaxial. If one knows the values of $C_1$ and $C_2$ and the load acting on the sample expressed in stress units, the intensity change can be directly related to the stress.

In the samples tested, the acoustic path was short, on the order of 2d (thickness of the sample) or 4d (3 or 6 mm in both aluminum and PMM). The small thickness of the samples causes the time difference between split wave components to be minimal, and in practice one can monitor only the superposition of these two mutually perpendicularly polarized components. These interfere with each other and cause intensity changes in monitored arrivals reflected from the bottom of the sample.

Figure 3:
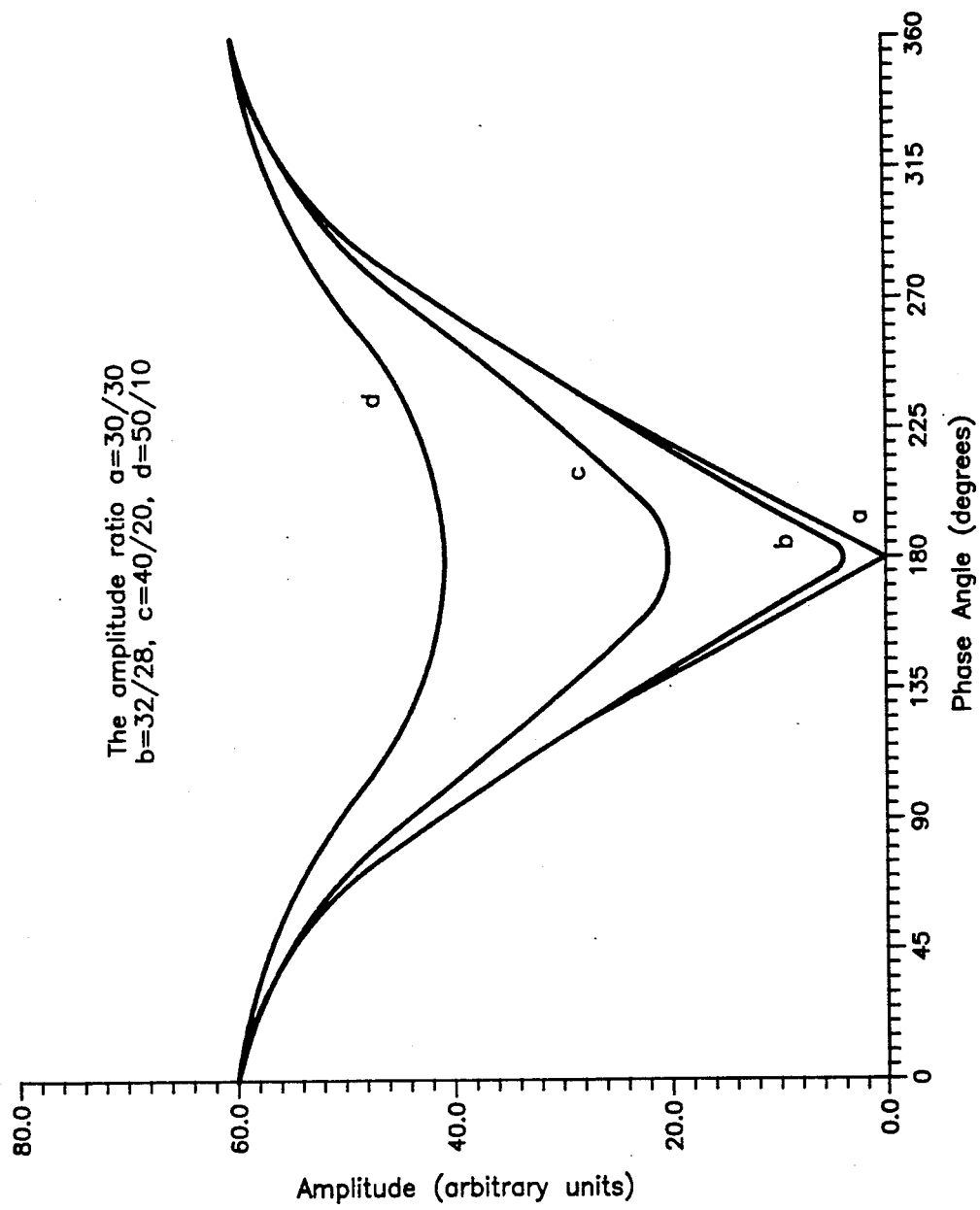
FIG. 3 is a diagram showing calculated resultant amplitude C, which is a sum of the amplitudes A and B of the two shear split components, as a function of the phase angle between them. Curve a represents the sum of two equally split components where $A=30$ mm and $B=30$ mm. Curve b is plotted for $A=32$ mm, $B=28$ mm. Curve c has two components $A=40$ mm, $B=20$ mm. Curve d was plotted for $A=50$ mm and $B=10$ mm. The amplitude of the two split components of shear wave depends on local stress distribution. The sensitivity of the amplitude variations (or the stress pattern contrast) increases with the phase angle between the components, and reaches its maximum at 180° degrees, and changes periodically for longer travel path. The acoustic imaging technique can always double or multiplay the travel path in the material tested by using for imaging the pulses after multiple reflections from the bottom and the top surface of the samples.

FIG. 3 shows the amplitude change as a function of increasing stress for different values of slower and faster components of shear waves. FIGS. 4c and 4b show the Mohr circles for different values of $\sigma_1$ and $\sigma_2$. The split of shear mode depends on actual state of stress in the sample. The sum of two vectors $C_1$ $$A \cos wt + B \cos(wt - \phi) = C$$

the amplitude C can be also expressed as $$C = [A^2 + B^2 + 2AB\cos\phi]^{\frac{1}{2}} \quad (6)$$

The resultant amplitude C calculated for different amplitudes A and B was plotted in FIG. 3.

The scanning acoustic technique measures the sum of amplitudes in the stressed area (FIG. 3). By taking different A and B for calculation one can see that when the state of stress changes at constant load, the intensity of monitored pulse will also change in comparison with the previous state.

The relative amplitude height of the shear mode, which measures the state and the magnitude of stress at the same time, must be calibrated by stress distribution calculation for quantitative values of the stresses in every point of the image. When the sample is in uniaxial state of stress, and when the propagation direction coincides with the direction of the principal stress, the acoustic imaging shows distribution of the shear stresses in scanning area, averaging the stress values over the thickness of the sample. When the sample is in biaxial state of stress, the magnitude of the acoustical birefringence is proportional to the sum or difference of the secondary principal stresses.

The software which was in use in this low frequency acoustic microscope imaging system has a single data gate, which has three adjustable parameters. The first is a gate start, which specifies an amount of time in the ultrasonic waveform. The second is the gate length, which specifies the amount of time after the gate start that the software will look for peaks in the waveform. The software looks for the highest value that the waveform attains. The waveform is RF, i.e. goes both positive and negative. The software does a rectification with no smoothing before doing the peak detection (takes the absolute value of the waveform). The third adjustable parameter of the data gate is a threshold, which specifies a percentage of full-screen height (FSH) of the oscilloscope waveform. If the peak falls below or is at this threshold, the corresponding pixel in the image is displayed as black. If the peak is at 100% FSH then the pixel is displayed as white. Peak values between the threshold and 100% FSH are displayed as a linearly corresponding grey value. The A/D board used in the system digitizes the voltage coming from the pulser/receiver. Being digital it clips signals sharply as with the scizors; there is no distortion or bowing of the waveform near 100% of FSH (usually 1V). So, whichever signal is in gate, or "window", the software will monitor the change of the amplitude of incoming signals, and the contrast of the image depends on the previous gate adjustment.

Figure 5:
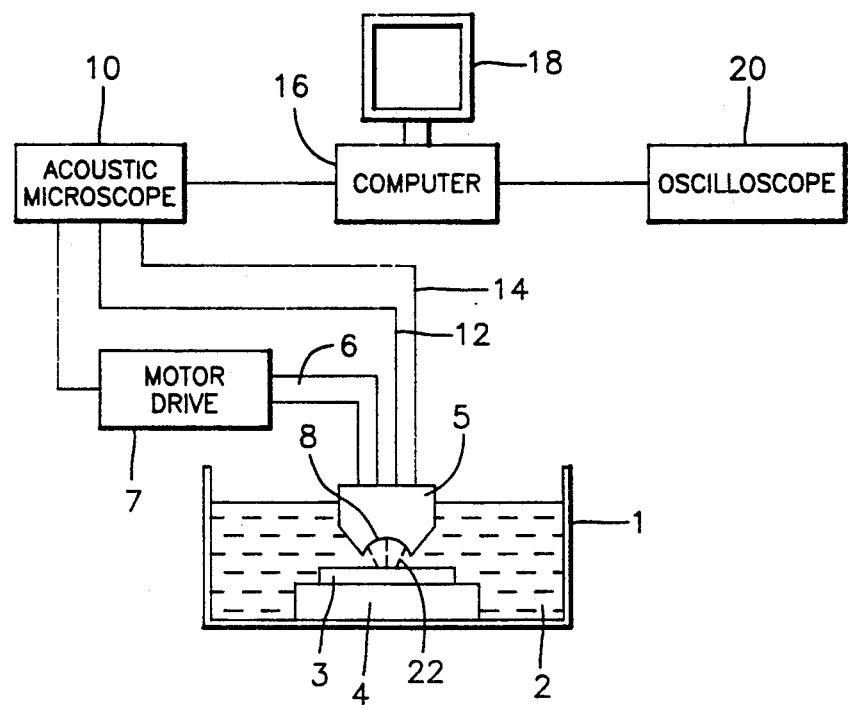
FIG. 5 is a schematic diagram of the system or apparatus of the invention.
Figure 6A:
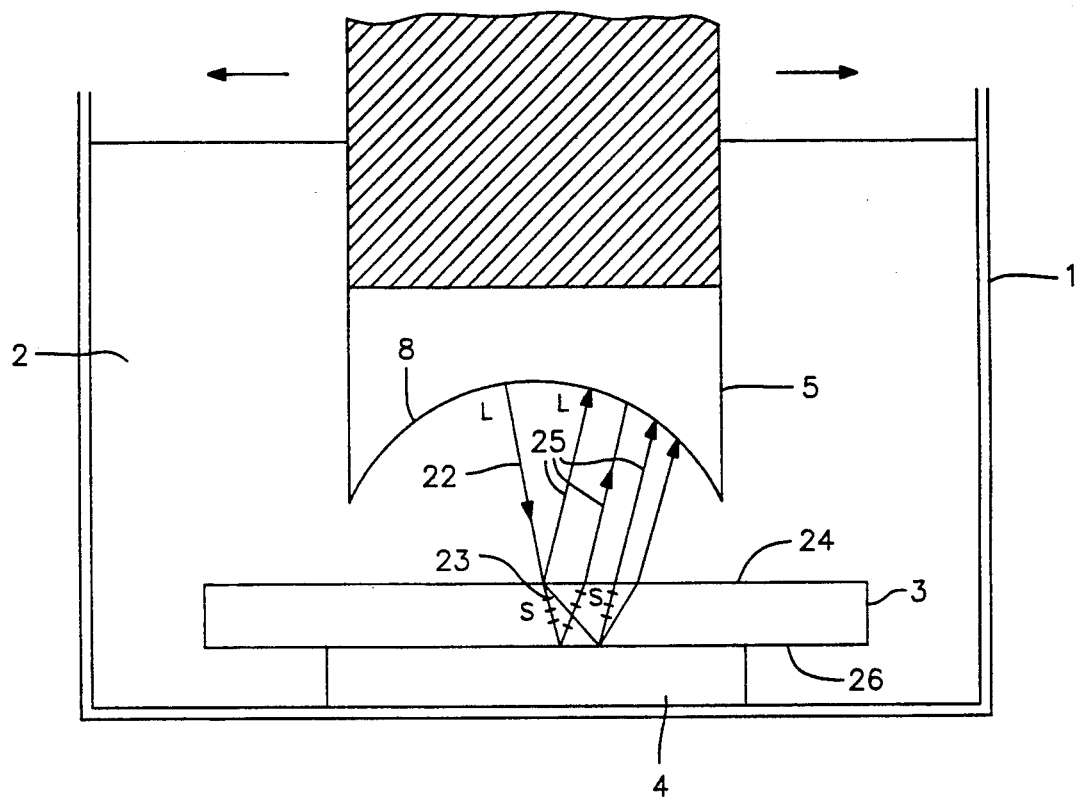
FIG. 6a is a schematic view of part of the apparatus showing the transmitted and received pulses by an acoustic microscope defocused lens in accordance with the invention. The sample of thickness d, was placed in the apparatus for compression with the surface of the sample parallel to the scanning plane. The first reflected pulse from the surface of the sample should be received at the same time over the whole scanning area. The time of arrival of this pulse serves also as a measure of the lens position toward the sample. Knowing the travel time, one can repeat the same experimental conditions. After the reflection of the longitudinal wave from the bottom of the sample the shear mode created by the reflection of the longitudinal wave at the bottom of the sample might be observed. Simple geometrical calculations of the time of arrivals allows to identify all observed modes at different position of the defocused lens.
Figure 6B:
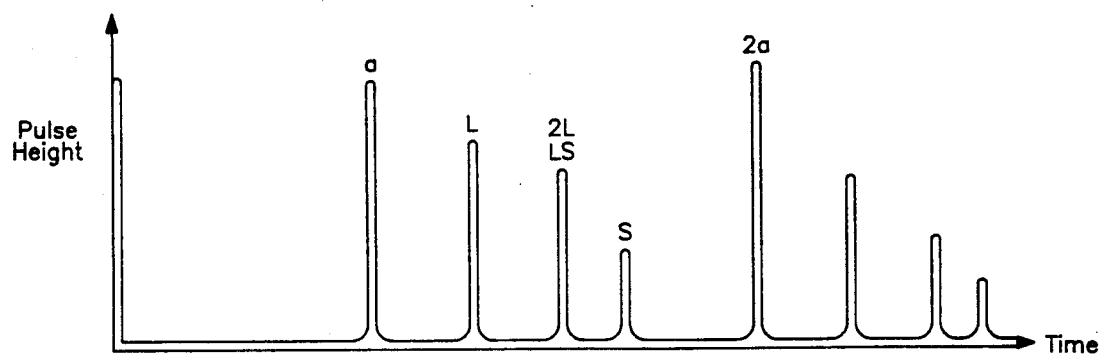
FIG. 6b is a chart showing pulse height as a function of time for received pulses.

FIG. 5 shows a schematic diagram of the apparatus, and FIG. 6a shows a part of the apparatus, of the invention for stress detection in samples of materials. A tank 1 contains a body of water 2 in which the sample 3 under investigation is immersed and supported either on the bottom of the tank 1 or on a support member 4, or in any other manner. An acoustic lens 5 is supported by an arm 6 of a motor drive unit 7 which is operable to move the lens 5 in the X, Y, Z directions for scanning over the sample 3. The lens 5 has a surface 8 having a spherical or circular cross-sectional concave shape from which the ultrasonic vibrations are transmitted and by which the echoes, or reflected ultrasonic waves are received. The lens surface 8 is designed to have a predetermined focal point as desired for the specific use intended. The motor drive unit 7 is a part of the acoustic microscope system 10 identified as MICROSCAN SYSTEM manufactured by SONIX, INC. Acoustic lens 5 has an integral ultrasonic transducer connected by lead wires 12, 14 to acoustic microscope 10 for transmitting ultrasonic waves, as best shown schematically in FIG. 6a, at 22 to the sample being tested and receiving the reflected waves 25 therefrom. The acoustic microscope is controlled by a computer 16 for exciting the transducer to produce the transmitted ultrasonic waves and to operate the motor drive unit 7 to move lens 5 in the X, Y and Z directions for scanning the sample.

Of course, sample 3 can alternatively be moved by a separate sample support device operable in the X, Y and Z directions, rather than moving with lens 5 for scanning.

The reflected ultrasonic waves 25 from the sample are received by lens 5 and converted to electrical signals which are used to ultimately display the acoustic microscope image of the stress patterns detected on screen 18. The image produced on screen 18 can be printed out as well known in the art.

Figure 4A:
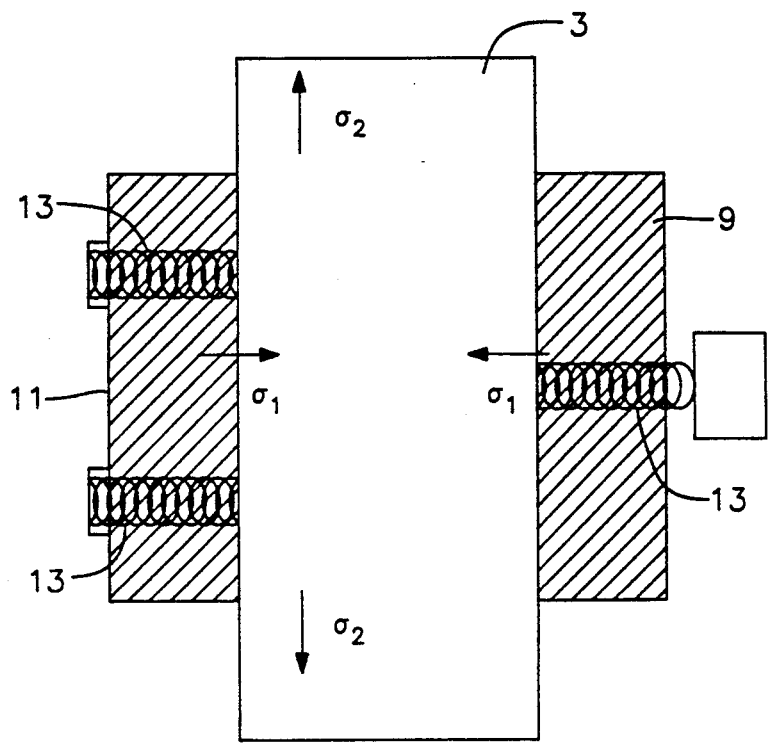
FIG. 4a is a schematic top plan view of a flat sample compressed between two rigid steel plates by a set of calibrating springs and screw devices.
Figure 4B:
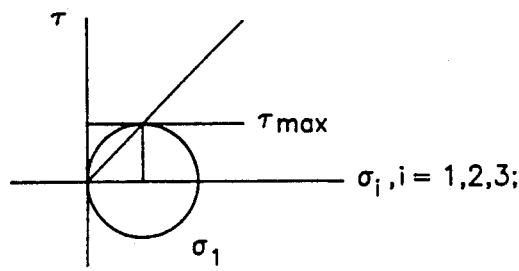
FIGS. 4b and 4c show Mohr circles having the values of shear maximal stresses in uniaxial (a) and biaxial (b) state of stress. The direction of propagation of the shear acoustic modes is perpendicular to the direction of the principal stresses and the acoustic image will reveal the distribution of the shear stresses in the compressed samples.
Figure 4C:
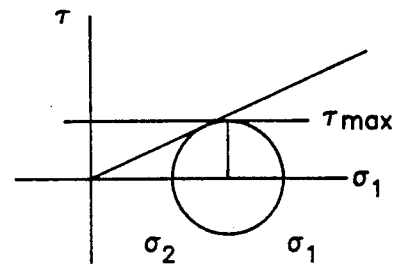

In examples of the invention, the sample is a flat, planar, plexiglass or aluminum sample 3 compressed between two rigid plates 9, 11 by a mechanical clamping device, for example (FIG. 4a). This experimental set up has a calibrated set of springs 13. By measuring the displacement of the springs and knowing the area of the sample subjected to compression the stress acting on the sample was calculated. The sample subjected to stress was placed in a water tank and the acoustic scanning system was adjusted to move parallel to the surface of the sample. The acoustic energy was sent to the sample through low angle acoustic microscope lens 5, and the same lens was used for receiving the signals. The polarized shear or polarized longitudinal modes reflected from the bottom of the sample (FIG. 6a) were selected for imaging. The shear mode can be excited and detected by the spherical acoustic microscope lens defocused below the surface of the samples (FIG. 6a). The plexiglass strip may be rectangular and have dimensions of 30×70×3 mm, with a longitudinal wave velocity of 2.7 min/msec and shear wave velocity of 1.1 mm/msec. Lens 5 has a frequency of 30 MHz and a focal point of 0.75 inches, which was defocused below the surface, i.e. the focal point was moved below the surface of the material of sample 3. The polarized shear mode is reflected from the bottom of the sample (FIG. 6a), and is excited and detected by the spherical acoustic microscope lens 5.

The shear mode 23, created by mode conversion at the water-solid interface 24, travels inside the sample, reflects from the bottom 26 of the sample (FIG. 6a) and according to Snell's law, converts its acoustic energy into the longitudinal mode at the solid-water interface. The efficiency of this conversion is calculated for every water-solid interface materials combination. Only the wave polarized perpendicularly, or at a certain angle to the plane of the sample surface will convert its energy into the longitudinal mode at the solid-water interface.

An oscilloscope 20 can be used in combination with the commercially available panning acoustic microscope 10 for measuring the time of arrival for the consecutive echoes reflected from the bottom of the sample. The oscilloscope may be a high frequency digitized scope with a frequency of 125 MHz (for example) and a time resolution up to 1 nanosecond for monitoring the ultrasonic arrivals as a function of time. Knowing the speed of shear and longitudinal waves in the material and measuring the sample's thickness it was possible to identify particular arrivals and choose the polarized modes for imaging. In all tests the acoustic microscope lens was always defocused, which means that its focal point was moved below the surface of the material. This is a necessary condition for creation of a shear wave propagating inside of the sample by mode conversion.

There is a variety of possible polarized modes and travel paths in the interior of the bulk material of the sample when it is considered that the ray will reflect from the bottom of the sample and convert from shear to longitudinal mode at the plexiglass-water interface. A sketch of all possible travel paths and the times of arrivals can be drawn in order to identify all ultrasonic pulses which might be monitored by the stress imaging. The fastest polarized shear arrival is shown in FIG. 6a. This ray is created by the reflection of the longitudinal wave at the small angle of the incidence from the bottom of the sample.

Figure 7A:
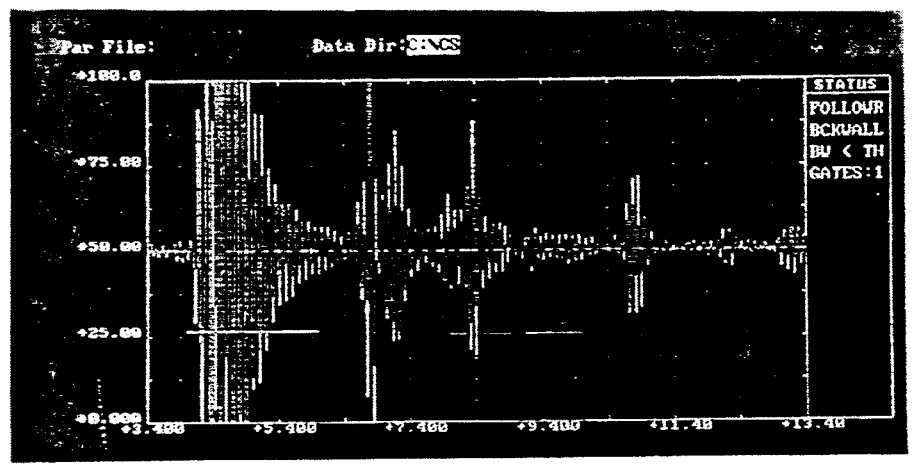
FIG. 7a and 7b are oscilloscope pictures showing possible arrivals from PMM and aluminum, respectively, samples monitored by the defocused acoustic lens. The curvature of the lens was 60° degrees, and the frequency used in the experiment was 10 MHz.
Figure 7B:
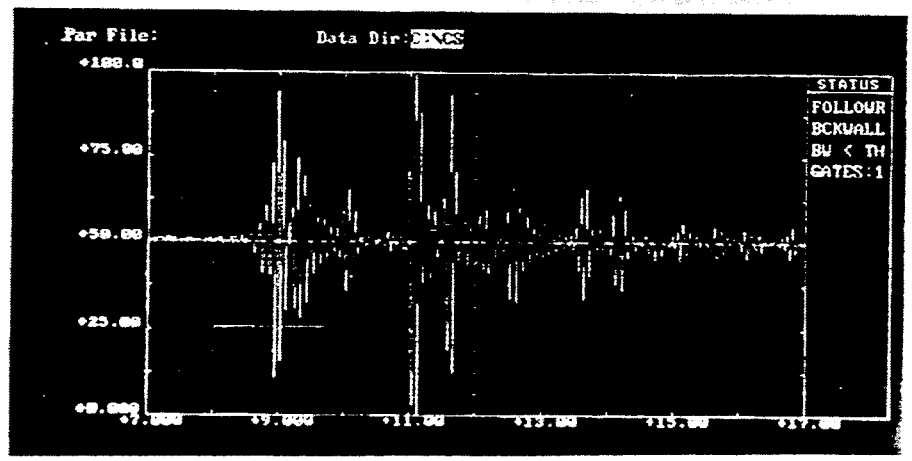

FIGS. 7a and 7b show the sequence of arrivals at the solid water interface for Plexiglass and aluminum, respectively, as a function of time calculated from the first water-solid reflection in an experiment conducted using a low frequency scanning acoustic microscope with a spherical, 10 MHz, 60° lens.

The acoustic modes in plexiglas are slow in comparison with the speed of sound in water. It should be noted, however, that the speed of a shear wave in plexiglas is comparable with the speed of a longitudinal wave in water. One can expect little or no contrast between these samples and water during shear wave imaging, as shown in FIGS. 5-10. The plexiglas samples were chosen because with this material defocusing a spherical, 60° degree lens does not excite a leaky mode between the sample and water, so that one can be certain that the differences in image intensity are caused by local stress concentration and not distorted by interference with the leaky mode propagating along the water-solid interface.

Figure 10:
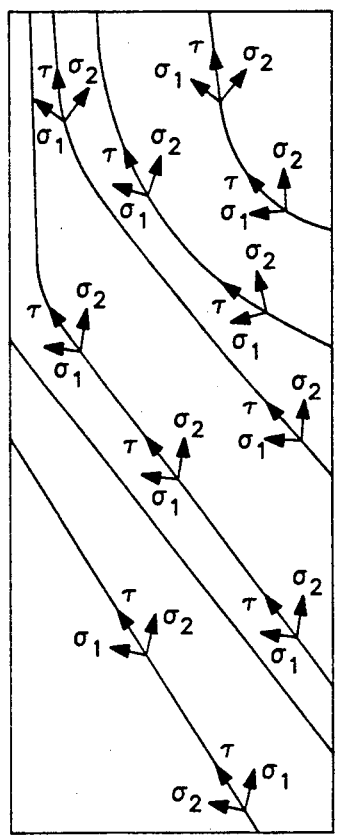
FIG. 10 is a schematic interpretation of the stress distribution in the sample under compression shown in FIG. 9. As illustrated by the Mohr circles, (FIG. 4) the maximum shear stress creates 45° angles with the direction of the two principal stresses.
Figure 8:
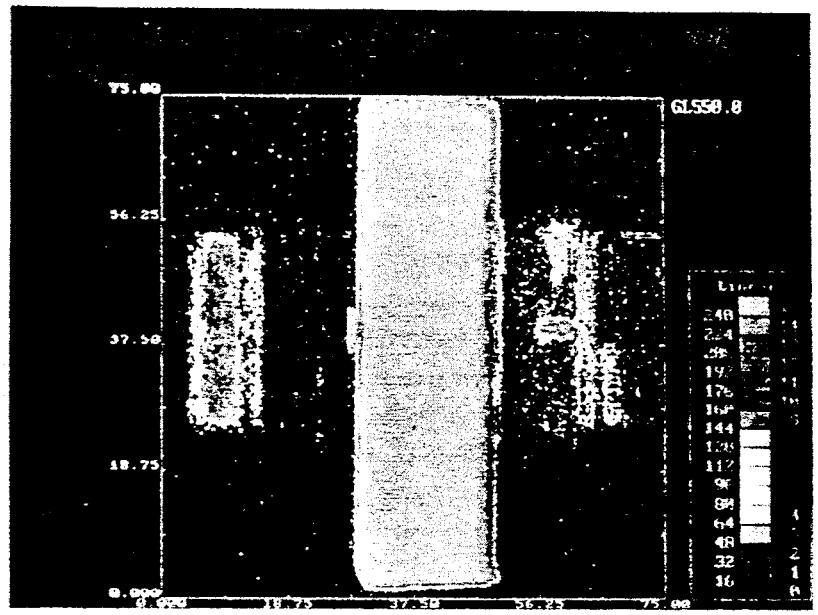
FIG. 8 is an acoustic microscope image made in accordance with the invention of the polymer sample scanned by use of the shear reflected mode (see FIG. 7a). The sample was placed in the apparatus for compression, but the stress was not applied yet. The intensity of monitored shear wave is constant over the whole scanning area. On both sides of the specimen, one can see the acoustic image of the two rigid steel plates and the set of screws.
Figure 9:
FIG. 9 is an image of the same sample as in FIG. 8 with the stress applied. The same shear mode shows during scanning the shear stress pattern over the whole area of the sample. In the lower part of the sample, where the compression is not applied the stress pattern is different then in between compressing plates.

The differences in image intensity in Pmm is caused by a local stress concentration and the lines seen on images are due to interference between the arrivals of reflected pulses from the bottom of the sample. FIG. 8 shows the plexiglas sample placed in the apparatus for compression, but the stress is not applied yet. The chosen shear mode for scanning does not reveal the stress presence in the volume of the sample. The whole area of the sample has homogeneous intensity. FIG. 9 shows the stress pattern after compression. The image was taken during the constant applied load. Certain areas of the sample demonstrate different intensities of the received pulses of the shear mode after reflection from the bottom of the sample. The wave length of shear mode at 10 MHz frequency is 0.11 mm in the plexiglas, and the applied stress is 11 MPa. From the calculations for Polythylene (FIG. 1) this amount of stress will cause the split of the shear wave into two components. If we assume that the birefringence effects are similar in Plexiglas, the difference in the speed between two shear components will be in the order of 3 m/sec for 11 MPa. Analyzing the stress distribution shown in FIG. 9 one can see that the sample is not in uniaxial or biaxial state of stress. Because the direction of the acoustic wave is perpendicular to the principal stress (or stresses) one can see the distribution of the shear stress over the volume and areas of the scan. FIG. 10 shows schematically the distribution of the principal stresses locally, in a few points of the image. Knowing that the maximum shear stress creates a 45° angle with the direction of the principal stresses the schematic picture of the stress distribution based on the acoustic scan is drawn.

Figure 11:
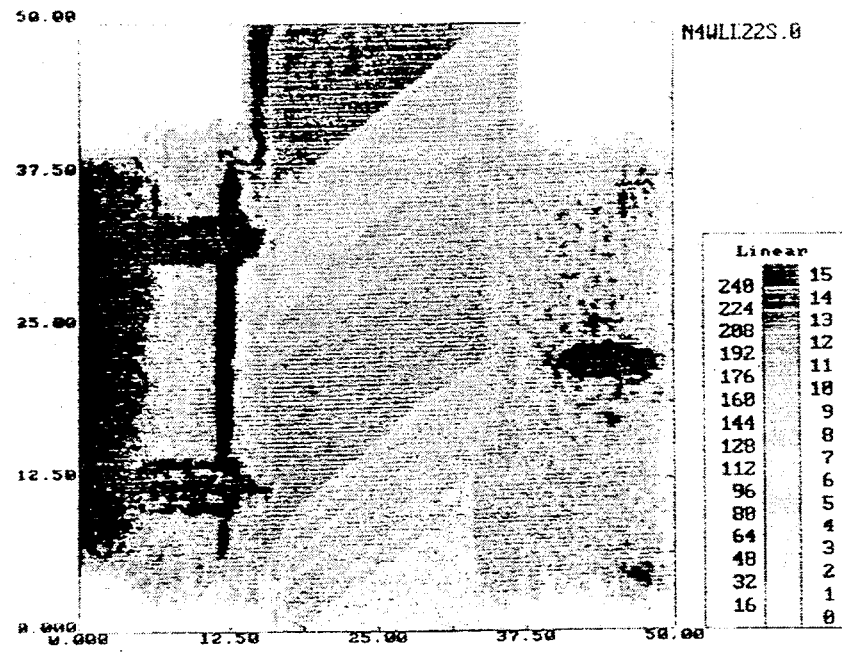
FIG. 11 is an image showing the sample of FIG. 8 under uniform uniaxial or biaxial stress after modification in the applied load. The direction of the maximum shear stress creates 45° angles with the direction of principal stresses. This image was obtained by monitoring the sum of the amplitude of the two shear polarized components (FIG. 3)

FIG. 11 shows a modification in the applied load. The friction on the edges of apparatus was decreased, and the stress pattern reveals homogeneous state of stress in the sample. The direction of the lines shows 45° degrees angle with the edges of the sample and the state of stress is homogeneous. The pattern reveals the distribution of shear stresses in the sample. The spacing between lines is in order of the thickness of the sample. The mechanism of the creation of these lines can be explained by interference condition:

$$2nd \cos r = (2m + 1)\frac{\lambda}{2}$$

where d is the thickness of the sample, r is the angle of refraction, n is the ratio of the speed of the longitudinal wave in water, and shear wave in PMM might be or 1.5/1.11=1.364, or if the refraction of longitudinal wave in polymer creates the polarized mode 1.5/2.7=0.555. The thickness of PMM sample was 3.04 mm, and the incident angle was close to 90°, so cosinus of the angle was close to 1. The interference will happene if the wave length of the shear mode will be a $m_1$ $$2nd \cos r = m \cdot \lambda; \text{ or } m\frac{\lambda}{2}$$

where m is an integer.

Figure 12:
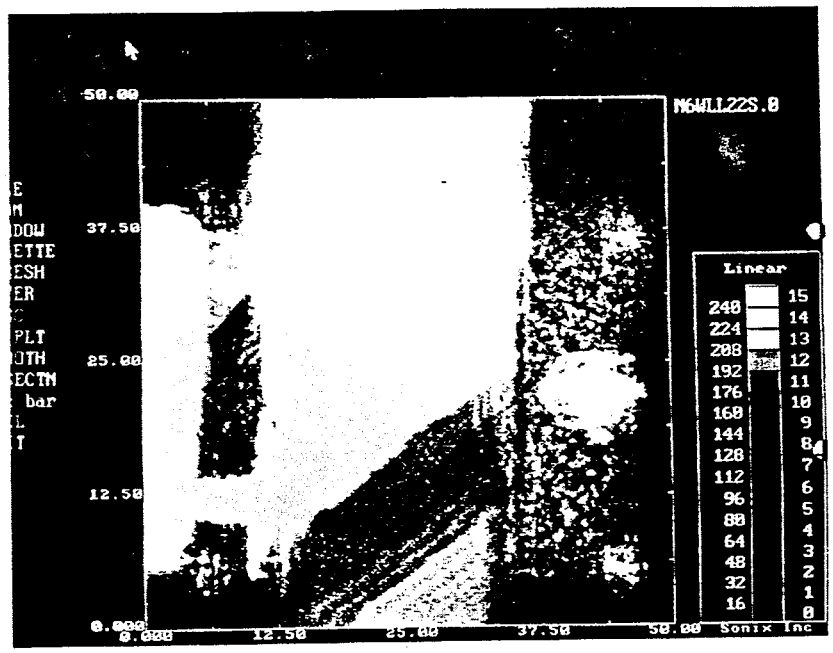
FIG. 12 is an image of the same state of stress in the sample of FIG. 11 (PMM). In this case the polarized longitudinal mode was used for scanning.

In certain areas of the image the lines are well defined. In these volumes of the sample the birefringence is constant, and the sum of the wave lengths is coherent with the thickness of the sample. With the increasing accuracy of the images it is expected to obtain the information on shear wave retardation directly from the image. Because the wave length in PMM is short, 0.11 mm at 10 MHz, and the resolution of printed images is low one can only estimate the separation between the lines. The value of the applied load corresponding to the phase angle shift in order of 50° degrees was 10.5 MPa. The acoustoelastic constant for PMM was not found in the literature. The interference of the reflected modes from the bottom of plane parallel samples can be used for an exact retardation measurement. In all interferometric methods one can adjust the travel path or the wave length to the condition when the wave length is coherent with the travel distance. This method is now in use for the calibration purpose and is described in E. Drescher-Krasicka and B. Tittmann, IEEE Ultrasonic Symp. 1992 (in preparation). As known, the acoustic waves propagating in anisotropic media experience the trirefringence effect. FIG. 12 shows the acoustic image of the same sample as above at the same state of stress taken by monitoring the intensity change of polarized longitudinal wave. In this case the wave retardation will be proportional to the sum of the secondary principal stresses. A similar pattern of the interference lines for shear and longitudinal modes leads to conclusion from (1) and (2) that:

$$\sigma_2+\sigma_3=\sigma_2-\sigma_3, \text{ so } \sigma_3=0$$

The sample is in uniaxial or biaxial state of stress.

Figure 13:
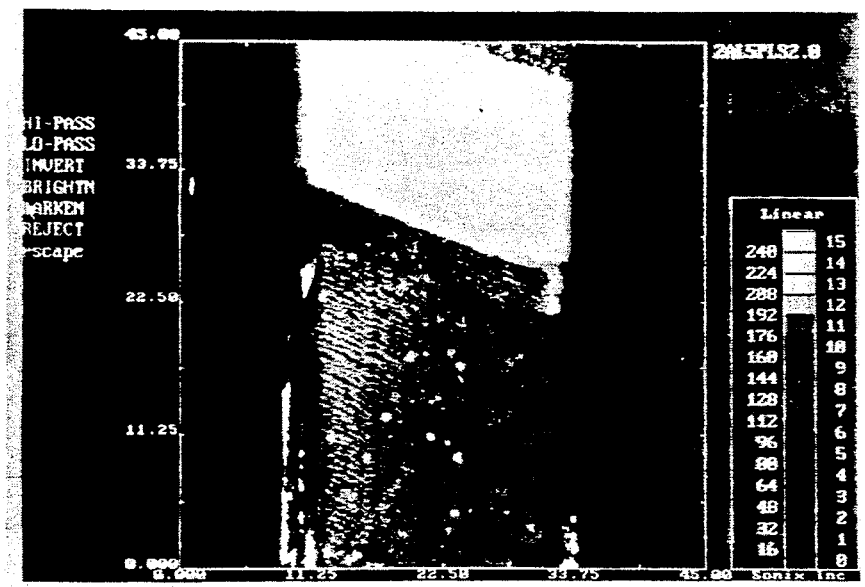
FIG. 13 is an image showing the distribution of stresses in the steel frame of the apparatus for compression. The mechanism of the line appearance has its source in the interference pattern with the path length of the acoustic wave.

FIG. 13 was made with the same experimental set-up, but the acoustic microscope gate was adjusted at longitudinal reflected wave arrival from the bottom of the sample. Coincidentally, there is a mode conversion into a shear polarized wave and birefringence effect caused by compression in the steel frame. The steel frame of the apparatus shows also similar shear stress pattern.

A second set of results was obtained for aluminum samples. Although the wave length of acoustic shear and longitudinal modes is relatively long in aluminum, the interference of leaky modes created at the water solid interface with the polarized shear mode arriving after reflection from the bottom of the sample causes visible patterns at the surface of the sample. In plane aluminum samples two distinguished patterns were observed in the stressed areas, an interference of the reflected polarized modes at the thickness of the sample and additional pattern of the interference with the leaky wave at aluminum/water interface. This can be used for the calibration purpose, because the phase velocity of the leaky modes at the interfaces can always be calculated for every solid/liquid or solid/solid interface (E. Drescher-Krasicka and J. A. Simmons, J. Acoust. Soc. Am., Pt. 2, (2), 1992; E. Drescher-Krasicka and B. Tittmann, IEEE Ultrasonic Symp. 1992 (in preparation)).

Figure 14:
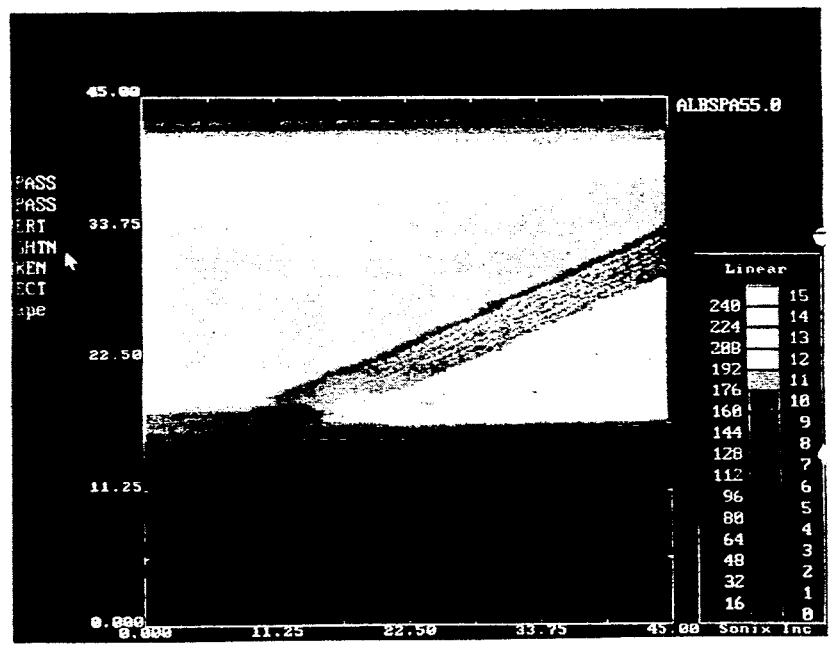
FIG. 14 is an acoustic microscope image of the aluminum sample scanned in the direction parallel to the applied stress in accordance with the invention.
Figure 15:
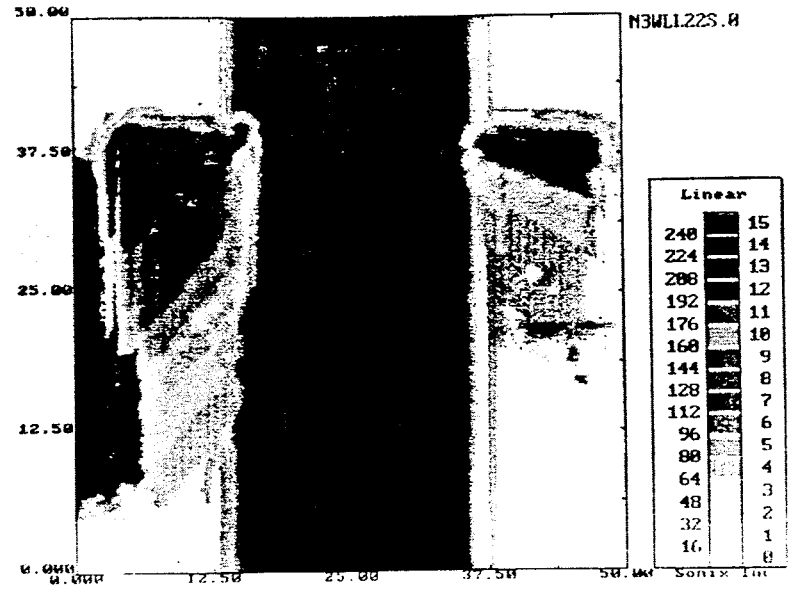
FIG. 15 is an image of the aluminum sample of FIG. 14 scanned in the direction perpendicular to the applied stress.

FIG. 14 presents an acoustic image of an aluminum sample scanned in the direction parallel to the applied stress. Due to internal stresses in the sample the resultant state of stress is very complex. FIG. 15 shows the same sample scanned in the direction perpendicular to the applied compression. Both figures are showing the lines where the interference of leaky and shear modes takes places. The angle of maximal shear stress shows that the direction of principal stresses does not coincide with the edges of the sample.

Figure 16:
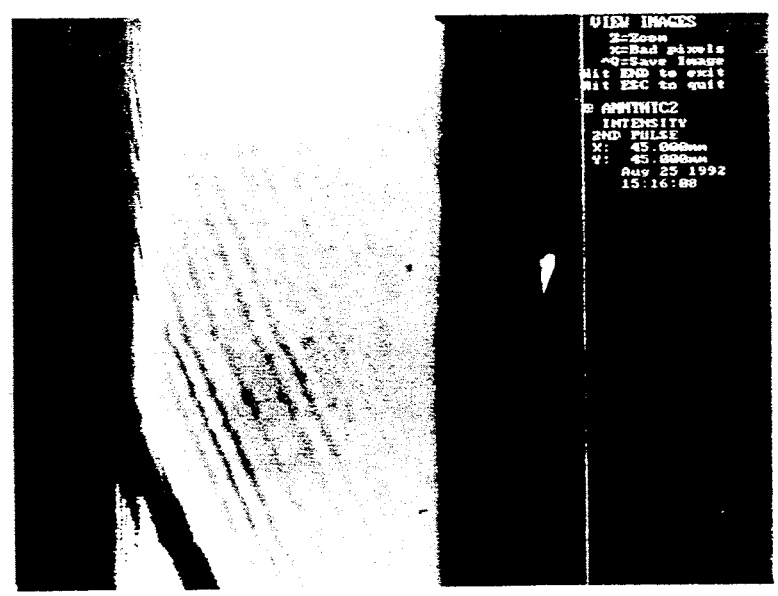
FIG. 16 is an acoustic image of the sample shown in FIG. 14 but, without stress and after annealing. The image reveals the residual stress field in the interior of the sample.
Figure 17:
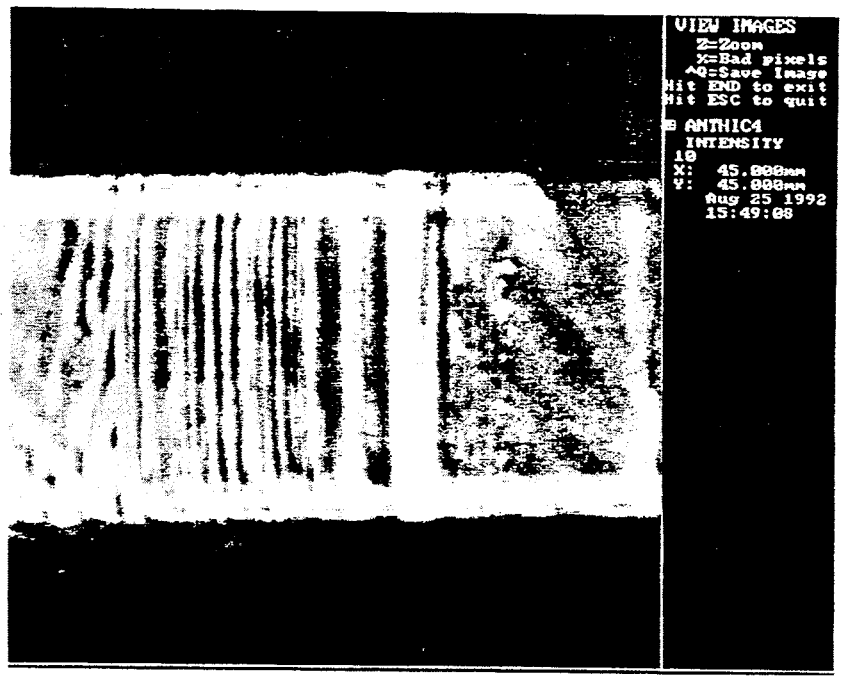
FIG. 17 is an image of the same sample as in FIG. 16, but the image was taken in the direction along the sample. After annealing and without the acting load the sample shown has a very complex state of residual stresses.

The sample was annealed and acoustic images were taken in the direction parallel and perpendicular to the sample as previously. The annealing and slow cooling did not remove the internal stresses caused probably by cold work in the aluminum sheet from which the samples were cut. (FIGS. 16 and 17).

Figure 18:
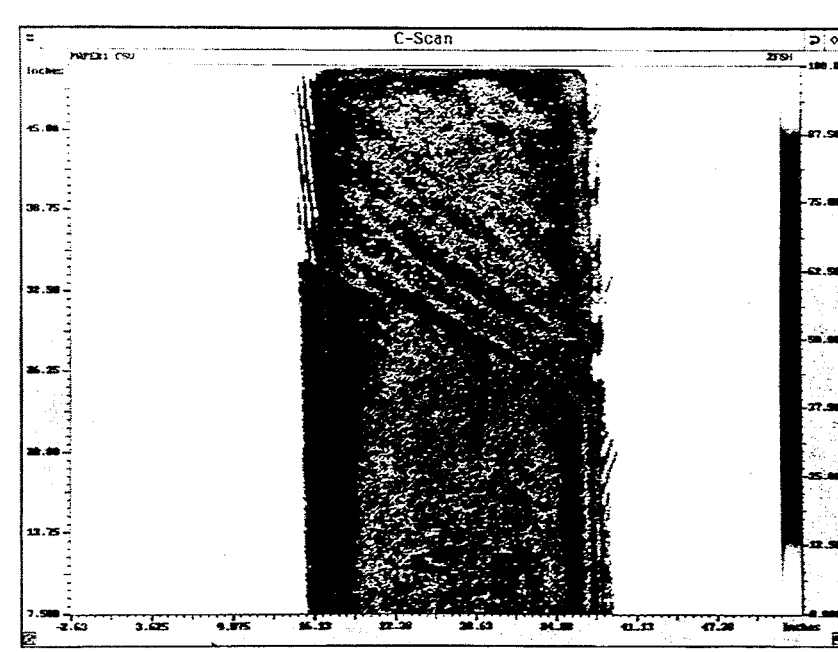
FIG. 18 is an image showing the actual state of stress in the aluminum sample, where the load was applied to the upper part of the sample only. The local shear stresses due to friction between the rigid plate and the sample are seen in the form of almost parallel lines of the spacing comparable with the shear wave length. The source of these lines is the interference between the surface leaky mode and the polarized shear wave in aluminum. The interior of the sample between the clamps reached quite a homogeneous state of stress, and the stress pattern created by the interference of the shear modes with the travel path for shear reflected waves filled up the area where the sample is tightly clamped. The rest of the sample does not reveal the presence of stresses.
Figure 19:
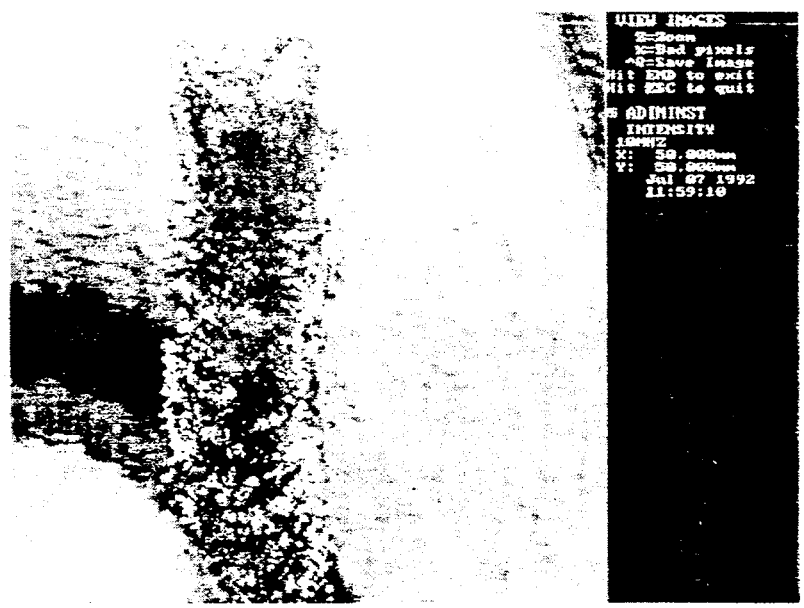
FIG. 19 is an image of an aluminum weld containing tungsten inclusion inside the weld. This inclusion is causing the stress field detected by the acoustic technique. The insert on the right hand side of the figure shows the X-ray picture of the inclusion inside this weld.

The stress imaging can also be used for evaluation of the state of stress in the sample placed between two rigid plates. The set of springs and screws applied the compression load at the edges of the sample. The scanned image (FIG. 18) shows the friction between the edges of the sample and the plates. The thin lines at the top of the sample visualize the shear stresses at the surface of the contact. The thick not very well resolved lines which repeat the thickness of the sample are filling the area of the sample where the relatively uniaxial compression is applied. The lower part of the sample is stress free. Another application of this technique is the detection of the stresses induced by defects in welds. FIG. 19 shows the image of aluminum weld with the tungsten inclusion in lower part of the image. The insert of FIG. 19 shows the X-ray picture of the tungsten inclusion in this weld. The internal stress in aluminum caused by inclusion shows the rings of different intensities. The thickness of the lines is comparable with the thickness of the sample.

Figure 20:
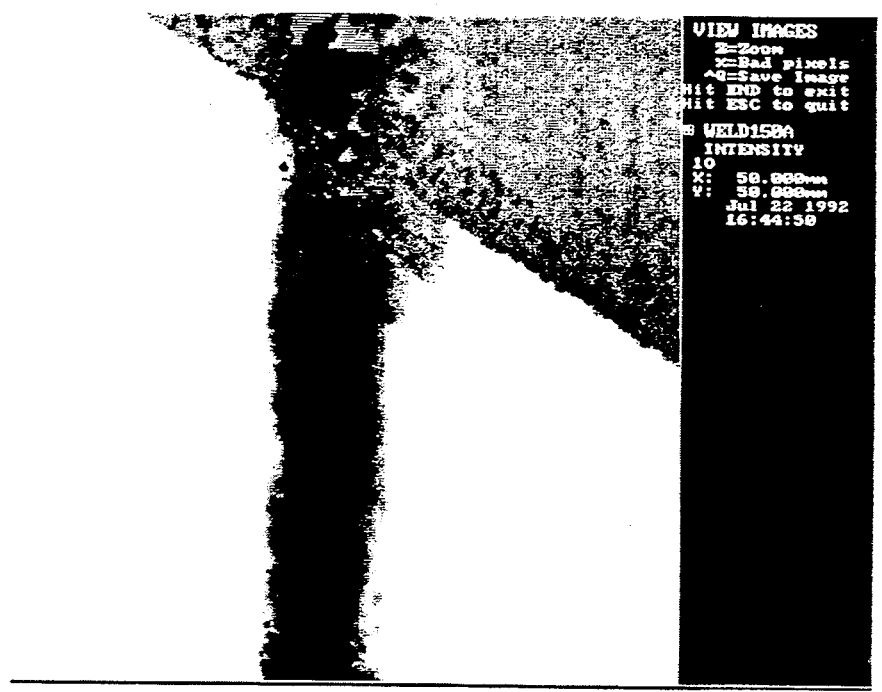
FIG. 20 is a further image of the inclusion inside the weld of FIG. 19, which causes the stress in welded materials. The X-ray of this weld confirms the presence of the inclusion.schematic diagram of the system or apparatus of the invention.

Similar situation of the inclusion causing the stress state in the welded materials is shown in FIG. 20. The insert of FIG. 20 shows the X-ray picture of the weld. The thick lines are of the size of the thickness of the sample (the pulse used for scanning was the shear reflected pulse from the bottom of the sample). The lowest line is filled up with the thin lines created by interference of shear modes with the surface leaky modes, but the resolution of the printer does not reveal this lines properly.

Acoustic imaging technique of this invention has been applied for stress detection in aluminum and plexiglass. Monitoring polarized modes amplitude change over the areas of plane samples subjected to compression reveals stress patterns. The observed intensity variations are related to acoustic trirefringence or birefringence which are analogous to photoelasticity. The stress pattern has quantitative features, and sonoelastic constants are known for every material tested.

Two different stress patterns were observed. The first is due to interference of polarized shear or longitudinal modes reflected from the bottom of the sample with the travel path length. The second is due to interference between polarized modes reflected from the bottom of the sample with the leaky interface waves at the surface of the aluminum. Both mechanisms were separated and demonstrated by use of the two materials with different elastic properties. The acoustic microscope lens (60°) was used for aluminum and plexiglass. This angle of incidence does not excite the leaky modes at the plexiglass/water interface, but always creates the surface leaky mode at the aluminum/water interface. The technique requires recognition of the polarized pulses and their times of arrivals in order to adjust the acoustic microscope time gate width and heights.

The invention is capable of detecting and imaging an instantaneous stress distribution pattern of the material tested. With the proper deconvolution method, the stored digitized data can be analyzed in order to directly translate intensity variations to the values of stress at every point of the image.

The foregoing description and accompanying drawings set forth the preferred embodiments of the invention at the present time. Various modifications, additions and alternative designs will, of course, become apparent to those skilled in the art in light of the foregoing teachings without departing from the spirit and scope of the disclosed invention. Therefore, it is to be understood that the invention is not limited to the disclosed embodiments but may be practiced within the full scope of the appended claims.

I claim:

1. A process for visualization of internal stress in solid materials by acoustic microscope imaging comprising:
   providing an acoustic microscope having an acoustic lens comprising an ultrasonic transmitter and an ultrasonic receiver;
   supporting a sample comprising a body of solid material to be examined;
   supporting said acoustic lens in spaced relationship to said sample;
   defocusing said lens by adjusting the focal point of said lens beneath the surface of said sample;
   exciting said ultrasonic transmitter to produce transmitted ultrasonic waves;
   directing said transmitted waves toward said body;
   positioning said acoustic lens relatively to said sample for receiving acoustic waves reflected from said sample and produced by said transmitted waves; and
   measuring the amplitude of said received waves to analyze distribution of internal stress in said sample.

2. The process as claimed in claim 1 and further comprising:
   choosing polarized shear modes produced in said sample in said received acoustic waves and separating said chosen shear modes from other received acoustic waves; and
   imaging the area beneath the surface of said sample by using said separated shear modes.

3. The process as claimed in claim 1 and further comprising:
   at least partially immersing said sample and said acoustic microscope lens in a liquid.

4. The process as claimed in claim 2 and further comprising:
   at least partially immersing said sample and said acoustic microscope lens in a liquid.

5. A process as claimed in claim 3 wherein:
   said liquid is selected from the group consisting of water and alcohol.

6. The process as claimed in claim 1 and further comprising:
   imposing a force on said sample to produce internal stresses therein.

7. The process as claimed in claim 3 and further comprising:
   imposing a force on said sample to produce internal stresses therein.

8. The process as claimed in claim 1 and further comprising:
   polarizing said waves; and
   controlling said transmitted waves to produce splitting of a polarized shear mode propagating through the material of said sample into at least two differently polarized shear modes having different velocities.

9. The process as claimed in claim 8 and further comprising:
   producing an acoustic microscope image using said at least two differently polarized shear modes separately.

10. The process as claimed in claim 4 and further comprising:
    applying an external force on said sample for producing at least one of tension and compression stresses in said sample.

11. The process as claimed in claim 1 and further comprising:
    polarizing said waves;
    controlling said transmitted waves to produce splitting of a polarized shear mode propagating through the material of said sample into at least two differently polarized shear modes having different velocities;
    producing quasi-longitudinal polarized modes in said sample; and
    producing an acoustic microscope image using at least one of said polarized modes.

12. An apparatus for visualization of internal stresses in solid materials by acoustic microscope imaging comprising:
   means for supporting a sample to be examined;
   ultrasonic transmitter means supported in spaced relationship to said sample support means for transmitting ultrasonic waves toward the sample;
   ultrasonic receiver means f or receiving ultrasonic waves reflected from said sample;
   motor drive means operatively connected to said transmitter and receiver means for moving said transmitter and receiver means with respect to said sample for scanning said sample;
   acoustic microscope means operatively connected to said ultrasonic transmitter means, ultrasonic receiver means and motor drive means for operating said motor drive means, exciting said ultrasonic transmitter means to produce said ultrasonic transmitted waves, and for receiving signals from said ultrasonic receiver means produced by said reflected waves so that said acoustic microscope detects differences in intensity of said reflected waves as an indication of internal stress in said sample; and
   computer means operatively connected to said acoustic microscope for controlling said acoustic microscope and receiving signals therefrom indicating said differences in intensity of said signals transmitted by said ultrasonic receiver and for visually displaying said signals from said acoustic microscope to show said differences in intensity.

13. The apparatus as claimed in claim 12 wherein:
   said ultrasonic transmitter means and ultrasonic receiver means comprise a unitary acoustic microscope lens for transmitting said ultrasonic waves and for receiving said reflected waves simultaneously.

14. The apparatus as claimed in claim 12 and further comprising:
   oscilloscope means operatively connected to said computer means and said acoustic microscope means for indicating said differences in intensity of said reflected waves as an indication of internal stresses in the sample.

15. The apparatus as claimed in claim 12 and further comprising:
   polarizing means for polarizing said transmitted ultrasonic waves.

16. The apparatus as claimed in claim 12 and further comprising:
   a tank containing a liquid; and wherein
   said sample, said ultrasonic transmitter means and said ultrasonic receiver means are at least partly immersed in said liquid.

17. The apparatus as claimed in claim 13 and further comprising:
   a tank containing a liquid; and wherein
   said sample, said ultrasonic transmitter means and said ultrasonic receiver means are at least partly immersed in said liquid.

18. The apparatus as claimed in claim 15 and further comprising:
   a tank containing a liquid; and wherein
   said sample, said ultrasonic transmitter means and said ultrasonic receiver means are at least partly immersed in said liquid.

19. The apparatus as claimed in claim 12 and further comprising:
   means for adjusting the focal point of said transmitted waves beneath the surface of said sample.

20. The apparatus as claimed in claim 12 and further comprising:
   means for measuring the amplitude of said reflected waves for analyzing distribution of internal stress in said sample.

* * * * *